United States Patent [19]

Reiner et al.

[11] Patent Number: 5,244,920

[45] Date of Patent: Sep. 14, 1993

[54] PHARMACEUTICAL COMPOSITIONS HAVING THERAPEUTICAL ACTIVITY BASED ON MERCAPTOETHANSULPHONIC ARGININE SALT

[75] Inventors: Alberto Reiner, Cantu; Giueseppe Vita, Segrate, both of Italy

[73] Assignee: Schering Spa, Milan, Italy

[21] Appl. No.: 960,216

[22] Filed: Oct. 13, 1992

Related U.S. Application Data

[60] Continuation of Ser. No. 676,407, Mar. 28, 1992, abandoned, which is a division of Ser. No. 348,171, May 2, 1989, Pat. No. 5,019,596, which is a division of Ser. No. 218,524, Jul. 7, 1988, abandoned, which is a continuation of Ser. No. 852,270, Apr. 15, 1986, abandoned.

[30] Foreign Application Priority Data

Apr. 15, 1985 [IT] Italy ................... 20338 A/85

[51] Int. Cl.$^5$ ............... A61K 31/205; A61K 31/85; C07C 9/00
[52] U.S. Cl. ................... 514/554; 514/578; 562/112
[58] Field of Search ............... 514/578, 554; 562/112

[56] References Cited

U.S. PATENT DOCUMENTS

| | | | |
|---|---|---|---|
| 2,694,723 | 11/1954 | Schramm | 260/501.21 |
| 2,695,310 | 11/1954 | Schramm | 260/501.21 |
| 3,567,835 | 3/1971 | Moner | 514/578 |
| 4,105,785 | 8/1978 | Ondetti | 260/501.12 |
| 4,220,660 | 8/1980 | Brock | 514/578 |
| 4,254,274 | 3/1981 | Tersada | 260/501.1 |
| 4,362,891 | 12/1982 | Guerrato | 260/501.1 |
| 4,418,206 | 11/1983 | Wren | 260/501.1 |
| 4,503,072 | 3/1985 | Hoffman | 260/501.1 |

OTHER PUBLICATIONS

Wilson "Textbook of Organic Medicinal and Pharmaceutical Chemistry", 7th Edition, p. 69 (1977).
Zehninger, "Biochemistry", 2nd Ed, pp. 71-76 (1970).
Sacha, C.A.:97: 127045b (1982).
Roccini et al, Advances in Urological Oncology and Endocrinology, Acta Medica, 1984 (pp. 391-397).

*Primary Examiner*—Frederick E. Waddell
*Assistant Examiner*—T. J. Criares
*Attorney, Agent, or Firm*—Nikaido, Marmelstein, Murray & Oram

[57] ABSTRACT

The L-arginine salts of the mercaptoethansulphonic acid are active in the therapy of the bladder carcinoma and in the therapy and prevention of the cistinic kidney calculi.

The saline derivatives with basic aminoacids and their alkyl esters are moreover devoid of side effects.

The latter derivatives are prepared by reacting, in aqueous or aqueous-alcoholic medium, equimolar amounts of mercaptoethansulphonic acid, just prepared from an organic or inorganic salt thereof, and of the desired aminoacid.

3 Claims, No Drawings

PHARMACEUTICAL COMPOSITIONS HAVING THERAPEUTICAL ACTIVITY BASED ON MERCAPTOETHANSULPHONIC ARGININE SALT

This application is a continuation of application Ser. No. 07/676,407 filed Mar. 28, 1992, now abandoned, which is a divisional of application Ser. No. 07/348,171 filed May 2, 1989, now U.S. Pat. No. 5,019,896, which is a divisional of application Ser. No. 07/218,524 filed Jul. 7, 1988, now abandoned, which is a continuation of application Ser. No. 07/852,270 filed Apr. 15, 1986, now abandoned.

The present invention relates to novel pharmaceutical compositions based on derivatives of the mercaptoethansulphonic acid, useful in the therapy of the bladder carcinoma and in the therapy and prevention of the cistinic kidney calculus. The present invention relates as well to novel organic saline derivatives of the mercaptoethansulphonic acid, having general formula:

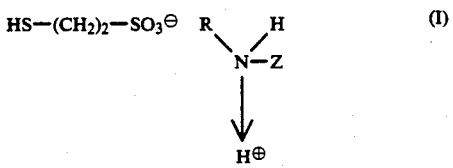

wherein R represents H,

and Z is the radical of a basic aminoacid or of a lower alkyl ester thereof, the aminoacid being particularly selected among lysise, in the L and DL forms, L-arginine, ornithine and cysteine, provided that when Z is the radical of L-arginine R is always

The invention furthermore relates to a process for the preparation of the above saline derivatives. The mercaptoethansulphonic acid is known from the therapeutical point of view as a mucolithic of the upper respiratory tract. However its administration can only take place by aerosol route. Owing to the high instability of this chemical compound it can not be taken into consideration in the free state, but only in form of a salt or other derivative, such as for instance the sodium salt. In this form it has been proposed and used both as mucolithic drug for the upper respiratory tract, and as antidote in the cases of haemorrhagic cystitis induced by antitumoral drugs (German published application No. 2756018 of Dec. 14, 1977, in the name of Astra Werke AG). Such a form however involved and still involves serious problem of saline balance in the organism, especially due to the high dosages used; for information purpose it is to be noted that the amount of sodium ions thus introduced in the organism may attain even 1000 equivalents over 24 hours.

It is thus evident that the above mentioned therapeutical effects do not and can not justify the drawbacks arising from the use of the sodium salt.

It has been now unexpectedly found that the mercaptoethansulphonic acid and the derivatives thereof capable of releasing it into the organism show a remarkable activity as antitumoral drug in the treatment of the bladder carcinoma. From experimental and clinical research work, carried out on patients affected by bladder carcinoma, either not previously treated with oxazaphosphorins or treated with these antitumoral drugs for nephrosic syndrome, the activity of the compounds of the invention was revealed both in preventing and in reducing the number of bladder relapses. In the patients affected by nephrosic syndrome, previous treated with cyclophosphamide and for whom the appearance of paraneoplastic phenomena in the bladder occurred, the mercaptoethansulphonic acid and its derivatives proved to be useful for their treatment.

As it is known from recent literature, tryptophan and its urinary metabolites act as indicators (markers) which are highly selective in the patients suffering from bladder carcinoma.

It has been now found that the administration of sodium mercaptoethansulphonate causes the normalization of the urinary levels of these metabolites in the thus treated patients.

It has been furthermore found, with like surprise, that the mercaptoethansulphonic acid and its derivatives as above defined are endowed with therapeutical activity in the prevention and in the treatment of the cistinic renal calculi. In fact the pharmacological and clinical tests demonstrated that these derivatives can dissolve concretions of cistinic nature.

In the most preferred embodiment of the present invention as the derivatives of the mercaptoethansulphonic acid useful for the above mentioned as well as for the other already known therapeutical uses there are foreseen the organic saline derivatives of the mercaptoethansulphonic acid corresponding to the preceeding formula (I) wherein R and Z have the above indicated meanings.

All the products of the salification between the mercaptoethansulphonic acid and the aminoacids according to the invention show well defined chemical characteristics, are water soluble with a pH of between 4 and 5, are not hygroscopic and show a slight smell characteristic of the thiolic groups —SH.

In turn the process for the preparation of the salts comprises the following steps:

1) Releasing the free mercaptoethansulphonic acid from an organic or inorganic salt thereof (the latter being prepared as described in J.A.C.S. 77, 6231 (1955) by M. Schramm, Lamoire and Karlson) through the use of a strong cationic resin, for instance Amberlite I.R.120, taking care of prevailingly operating under nitrogen stream and at a temperature of between 5° C. and 10° C. in order to prevent thiolic bonds from being formed.

2) Reacting equimolar amounts of mercaptoethansulphonic acid and of basic aminoacid in aqueous or hydroalcoholic medium, then concentrating the reaction mixture until a solution of containing about 80% of the active substance is obtained and lastly crystallizing from absolute ethanol the desired salt.

3) After filtration, washing and drying, hot dissolving the salts into a diluted water-alcohol solution, the salts being then slowly crystallized under stirring.

From the preceeding description it clearly appears that, according to a first feature of the invention, both the known and the novel derivatives of the mercaptoethansulphonic acid are endowed with a therapeutical activity both towards the bladder carcinoma and towards the cistinic renal calculi, the novel organic saline derivatives according to the invention being preferred as being free from the side problems and drawbacks arising in the case of the known derivatives of the subject acid.

According to another feature of the invention organic saline derivatives of the mercaptoethansulphonic acid are provided which are more useful than the known ones or, to say better, exempt from the already mentioned problems and drawbacks of the known derivatives.

For sake of comparison the data of acute toxicity as found for some organic saline derivatives of the invention and for the sodium salt of the mercaptoethansulphonic acid are hereinafter reported:

sodium salt $LD_{50}=2080$ mg/kg
salt of L-arginine $LD_{50}>2000$ mg/kg
salt of DL-lysine $LD_{50}>2500$ mg/kg.

As regards the stated therapeutical activity of the compounds of the invention, experimental work as been carred out both in vitro and in vivo as hereinafter shortly reported.

The interest for the urinary tryptophan (Trp) methabolic profile in bladder cancer patients, has shown a steady increase parallel to the experimental research which continues to evidence not only the close structural and stereochemical similarity between some bladder chemical carcinogens and certain Trp metabolites, but also the powerful cancerogenicity of some of these. Particular preminence here is deservedly given to anthranilic (AA) and 3-hydroxy-anthranilic acid (3-OH-AA). Both have been found in high concentrations in the urine of bladder cancer patients (Quagliariello E., Tancredi F., Fedele L., and Saccone G., Tryptophan-nicotinic acid in patients with tumors of the bladder; changes in the excretory products after nicotinamide and vitamin B6. Brit. J. Cancer 15:367-372, 1961; Boyland E., and Williams D. C., The metabolism of Tryptophan in patients suffering from cancer of the bladder. Biochem. J. 64:578-582, 1956; Brown R. R., Price J. M., Satter E. J. and Wear J. B. The metabolism of Tryptophan in patients with bladder cancer. Acta Unio Intern. Contra Cancrum 16:299-303, 1960.

The discovery of free AA, usually not detectable except in glicuroconiugated form, has aroused special interest. Both cigarette smoke or the lack of pyridoxinic (B6) coenzymes can increase its excretion blocking the anthranalic acid conversion to quinalic acid. Anthranilic acid produced by the (hepatic) nicotinic-acid pathway, is in any case immediately coniugated with glicuronic acid and which such excreted. The recovery of urinary free-AA probably suggests an intra-bladder increase of beta-glicuronidases levels (from chronic flogosis, parasitic inflammation etc..) which would separate in this way the glicuronide. Anthranilic acid and its ortho-hydroxy derivative (3-OH-AA) are structurally similar to 4-aminophenyl, a chemical bladder cancerogen, and could (as suggested by Pipkin G., and Schlegel J. U. Decomposition of 3-hydroxyanthranilic acid under simulated physiologic conditions. P.S.E.B.M.120-592-595, 1965) excercise not only a direct oncogenic action but also be later degraded to metabolites more and more powerful (orthoN-hydroxy methyl derivatives). In effect the, intrabladder implantation of pellets containing AA and 3-OH-AA, has allowed Bryans and co-workers (Bryan G. T., Brown R. R. and price J. M. Mouse Bladder cancerogenicityof certain Tryptophan metabolites and other aromatic nitrogen compounds suspended in cholesterol. Cancer Res. 24:596-602, 1964) to induce a neoplastic growth in the majority of animals.

Recently, it has been observed, Rocchini P., Bizzarri M., Tenaglia R., and Di Silverio F. Urinary and plasma levels of Tryptophan and related metabolites in bladder cancer patients. In: Advances in Urological Oncology and Endocrinology; Edited by Bracci U. and Di Silverio F., Acta Medica Edizioni e Congressi, p. 410, 1984) in patients suffering from bladder tumor, how, after many months since the transuretheral (TUR) treatment, the urinary excretion of Trp metabolites remained almost unchanged. In that work it was emphasized how the presence of high urinary anthranilic acid levels costituted a permanent oncogenic stimulus, in some way, correlative to the heterotopic recurrences frequently observed in these patients.

The experiments were carried out with arginine mercaptoethansulphonate (hereinafter indicated by MESNA-arginine)

a) "in vitro" experiments

1) In order to estimate the supposed bonding power of MESNA (mercaptoethansulphonic acid) in respect to the AA and 3-OH-AA a series of in vitro experiments was initially carried out. Known quantities of AA and 3-OH-AA (standard 99.0% pure, obtained from Sigma Chem. Corp.) were dissolved in phyiological solution (pH 7) and thermostated at 37.5° C. MESNA-Arginine in equimolar ratio to AA and 3-OH-AA was subsequently added.

2) The bonding power of MESNA was subsequently tested in 24 hours urine samples obtained from bladder cancer patients; 18 test-tube of urine were set-up and randomized in three groups; to 6 samples was added MESNA in equimolecular ratio to AA and 3-OH-AA, previsouly determined by HPLC; another 6, after the MESNA addition, were thermostated at 37.5° C. for 12 hours; the remaining 6, thermostated at 37.5° C. were kept as control.

b) "In vivo" experimental trial 24 bladder cancer patients were randomized into two groups to receive MESNA-Arginine (per os, 800 mg/daily) or placebo. In both groups 24 hours before and after administration of the drug (MESNA-Arginine, or Placebo), urinary Kynurenine (Ky), Xanthurenic acid (XA), 5-hydroxy-indoleacetic acid (5-HIAA), AA, Trp and 3-OH-AA were determined by HPLC in reverse phase (Rocchini P., Bizzari M., Pompei M; Ciani D., Panicucci M. and Gallo S. Urinary determination of Tryptophan and related metabolites through HPLC in reverse-phase. Rass. Chimi. 1:15-18, 1984.)

Results a) "in vitro" experiments

1) From the solution's chromatograms, before and 2 hours after MESNA addition a significative reduction (P-0.001) of AA (−29%) and 3-OH-AA (−42%) concentration as well as the presence of a third (MESNA+3-OH-AA) and a fourth (MESNA+AA) peak was recorded. It was noticed that the same determinations were carried out in duplicate with two samples of the physiological solution in which AA and 3-OH-AA were dissolved without addition of the drug. In this case no chromatographic variations related to AA and 3-OH-AA concentration were observed.

2) In all the thermostated samples, following the addition of the drug, anthranilic and 3-hydroxy-anthranilic acid completely disappeared after a 6 hours interval. In the urine sample additioned with MESNA and assayed at room temperature there was noticed a consistent decrease which becomes almost complete only after 12 hours. No statistically significant changes were observed in the control samples.

b) "in vivo" experimental trial

All MESNA-Arginine treated patients showed, after a 24 hours interval, a significative (P-0.001) reduction of anthranilic (−61%) and 3-OH-anthranilic acid (−71%); a slight reduction of the urinary tryptophan levels was also observed; no variation of the kind was evidenced for kynurenine, xanthurenic acid or 5-HIAA. No significant modifications in urinary Trp metabolites values were observed in the placebo group.

Results reported above suggest that MESNA-Arginine blocks-up AA and 3-OH-AA "in vitro" as well "in vivo".

The incomplete disappearance of the two metabolites, as opposed to that noticed in vitro, can be explained by the fact that the reaction MESNA+AA and MESNA+3OH-AA occurs in the equimolecular ratio. The administration of the drug at standard doses may not ensure a complete interaction with the two metabolites, the levels of which changes considerably from case to case; moreover it cannot be excluded that changes of the urinary pH, as well as the presence of other reacting chemical groups, may interfere with the durg.

Activity of MESNA-arginine was strictly limited to the urinary tract. In fact no variations relating to the cerebral uptake of Trp were recorded as it is documented by the substantial invariance in the rate excretion of 5-HIAA; and so much the reduced excretion of metabolites relating to the nicotinic-acid pathway has been withness the unchanged Ky and XA excretion rate. The carboxylic group of AA and the oxydrylic group of 3-OH-AA are probably concerned in the matter.

As regards the therapeutical uses of the novel organic saline derivatives according to the invention their administration takes place either orally and/or by intravenous route at doses remarkably less than the above indicated toxicity values. The dosage levels used in the therapy and prevention of cistinic kidney calculi are generally the same as the dosage levels used in the therapy of bladder carcinoma. These dosage levels are generally in the range of 300 to 1200 mg/day, preferably about 800 mg/day.

As regards the pharmaceutical forms there are provided capsules, tablets, granules, suppositories, syrups, normal and lyophilized vials or ampoules for intravenous, intramuscolar, topical and aerosol use; the preparation of the pharmaceutical compositions is carried out according to the normal pharmaceutical techniques and using the normal solvents, diluents, excipients and vehicles. Some examples are hereinafter provided, having illustrative but non limiting purpose, relating to the preparation of the organic saline derivatives according to the invention.

EXAMPLE 1

Preparation of (DL)-lysine mercaptoethansulphonate

The mercaptoethansulphonic acid is freed from an inorganic or organic soluble salt thereof in a chromatographic column by means of Amberlite IR 120 resin; in the specific case 12 g of sodium salt of mercaptoethansulphonic acid, corresponding to 10.4 g of free acid, are dissolved in an aqueous solution having pH 4.9 at a 10% concentration under a stream of pure nitrogen. Then this solution is passed through the column with a flow rate of 80 mg/h. The aqueous solution of the acid comes out of the column at pH=1. In order not to leave the mercaptoethansulphonic acid in acidic solution, wherein the degradation thereof might take place a nitrogen stream is passed and simultaneously a 25% aqueous solution of DL-lysine in free base form in a stoichiometrical amount (10.7 g) is added.

The addition rate is adjusted so as to operate at pH values of between 6.5 and 5.5. Upon the salification is completed the pH of the solution of the salt must be of between 5 and 6. The solution is then concentrated to about dryness under vacuum giving place to a white-yellowish residue which is taken with 99% methanol and refluxed for 15 minutes; then it is cooled down and filtered. There are obtained 17.5 g of salt having melting point of 180°–186° C. The methanolic waters are concentrated to dryness and taken with fresh methanol, whereby 2.5 g of product having m.p. 180°–186° C. are further recovered. The two products are combined and refluxed again for 15 minutes in 100 ml of 99% methanol. The mixture is cooled under stirring and filtered giving place, after drying in an oven at 50° C., to 17.8 g of white crystalline product having melting point 193°–194° C. The yield is 85% of the theoretical value, the pH in 10% water solution is 3.95 and the solubility in water is perfect. The analysis gave the following results:

| Theoretical | Found |
|---|---|
| C = 33.32% | 32.06% |
| H = 6.99% | 7.09% |
| N = 9.71% | 9.68% |

EXAMPLE 2

Preparation of arginine mercaptoethansulphonate 12 g of sodium mercaptoethansulphonate are freed in aqueous solution and under nitrogen stream in a column, as described in the example 1. The mercaptoethansulphonic acid coming out of the column in aqueous solution, under nitrogen stream and at pH=1, is gradually added with arginine, in free base form, in stoichiometrical amount dissolved in water under nitrogen stream (12.7 g), by operating at pH values of between 6 and 7. Upon the salification is completed the pH of the solution of the salt must be of between 6 and 7. The solution is then concentrated to dryness giving a residue which, upon being taken with 200 ml of absolute ethanol, under stirring and in hot condition, is converted into white crystals. The suspension is agitated at 50° C. for 30 minutes, then cooled and filtered, whereby 22.8 g of white crystalline product are obtained, with a 98% yield and a melting point of 214°–216° C.; the pH in 10% aqueous solution is 6.7 and the solubility in water is perfect. The analysis gave the following results:

| Theoretical | Found |
|---|---|
| C = 30.37% | 30.16–30.40% |
| H = 6.37% | 6.43–6.48% |
| N = 17.71% | 17.54–17.69% |

EXAMPLE 3

Preparation of L-ornithine mercaptoethansulphonate 0.8 g of sodium mercaptoethansulphonate in aqueous solution and under nitrogen stream are freed in a chromatographic column, as described in the example 1.

The mercaptoethansulphonic acid coming out from the column, in aqueous solution, under nitrogen stream and at pH=1, is simultaneously added with the stoichiometrical amount of L-ornithine (0.64 g) freed from the hydrochloride through Kastel A 300 resin, in aqueous solution and under nitrogen stream. The addition is carried out at pH values of between 6 and 7. Upon the salification is completed the pH of the solution must be of between 5 and 6. The solution is concentrated to about dryness giving place to a colorless oil which is hot taken with 10 ml of 99% methanol. A conversion to white crystal takes place and the mixture is filtered and dried in oven under vacuum 1.117 g; yield 85%; m.p. 187°–192° C; the pH in 10% aqueous solution is 4.2 and solubility in water is perfect. The analysis gave the following results:

| Theoretical | Found |
|---|---|
| C = 30.64% | 30.39–30.65% |
| H = 6.61% | 6.67–6.76% |
| N = 10.21% | 10.04–10.20% |

Preparation of mercaptoethansulphonate of crysteine methylester 0.5 g of sodium mercaptoethansulphonate are freed as described in the preceeding examples; then, as the mercaptoethansulphonic acid comes out from the column, it is salified with the stoichiometrical amount (0.53 g) of L-crysteine methylester hydrochloride, is dissolved in pure methanol and added with sodium hydroxide dissolved in methanol; by filtration the sodium chloride is separated and the alcoholic solution is added simultaneously to the aqueous solution of mercaptoethansulphonic acid. The salification is carried out at a pH of between 5 and 6.

Upon the salification is completed the pH must have a value of between 4.5 and 5. The water-alcohol solution is concentrate to dryness giving a clear colorless oil, which, taken with absolute ethanol and refluxed under stirring for 15 minutes, is converted into white crystals.

Dry product: 0.626 g; yield 73%; water soluble; the pH in 10% aqueous solution is 4.6. The melting point can not be determined since the product undergoes a transformation when the temperature is increased up to 280° C. In the above description specific reference has been made to the saline derivatives of the mercaptoethansulphonic acid with basic aminoacids and their alkylesters, as well as to the sodium salt, but it is to be meant that the scope of the invention, as regards the novel therapeutical uses, i.e. therapy of the bladder carcinoma and therapy and prevention of the cistinic renal calculi, is to be considered as extended to all the derivatives capable or releasing in the organism mercaptoethansulphonic acid.

We claim:

1. An organic salt of mercaptoethansulphonic acid represented by the formula:

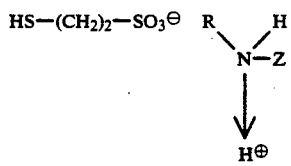
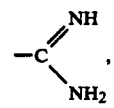

wherein R is

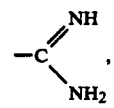

and Z is the radial of L-arginine or lower alkyl esters of L-arginine.

2. A pharmaceutical composition for the treatment of bladder carcinoma, comprising an anti-tumor effective amount of an organic salt of mercaptoethansulphonic acid represented by the formula:

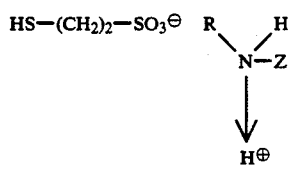

wherein R is

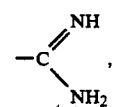

and Z is the radial of L-arginine or lower alkyl esters of L-arginine and a pharmaceutically acceptable carrier.

3. A pharmaceutical compositions for the treatment of cystinic kidney calculi, comprising an anti-calculi effective amount of an organic salt of mercaptoethansulphonic acid represented by the formula:

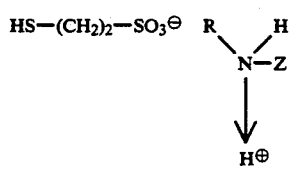

wherein R is

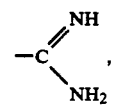

and Z is the radial of L-arginine or lower alkyl esters of L-arginine and a pharmaceutically acceptable carrier.

* * * * *